United States Patent
Wenzel et al.

(10) Patent No.: US 6,720,710 B1
(45) Date of Patent: Apr. 13, 2004

(54) MICROPUMP

(75) Inventors: Stuart W. Wenzel, Kensington, CA (US); Benedict J. Costello, Berkeley, CA (US)

(73) Assignee: Berkeley Microinstruments, Inc., Richmond, CA (US)

( * ) Notice: Subject to any disclaimer, the term of this patent is extended or adjusted under 35 U.S.C. 154(b) by 0 days.

(21) Appl. No.: 08/779,545

(22) Filed: Jan. 6, 1997

Related U.S. Application Data (60) Provisional application No. 60/009,665, filed on Jan. 5, 1996.

(51) Int. Cl.[7] .............................................. H01L 41/08
(52) U.S. Cl. ........................................ 310/328; 417/474
(58) Field of Search ......................... 310/326, 8, 324, 310/323.02; 417/474, 475, 413.2, 321

(56) References Cited

U.S. PATENT DOCUMENTS

| | | | | |
|---|---|---|---|---|
| 4,632,311 A | * | 12/1986 | Nakane et al. | 239/101 |
| 5,006,749 A | | 4/1991 | White | 310/328 |
| 5,096,388 A | * | 3/1992 | Weinberg | 417/322 |
| 5,215,446 A | * | 6/1993 | Takahashi et al. | 417/322 |
| 5,466,932 A | | 11/1995 | Young et al. | 250/289 |
| 5,525,041 A | | 6/1996 | Deak | 417/63 |
| 5,812,163 A | * | 9/1998 | Wong | 347/68 |
| 5,906,481 A | * | 5/1999 | Ogawa et al. | 417/413.2 |
| 6,076,408 A | * | 6/2000 | Matsubara et al. | 73/714 |
| 6,198,203 B1 | * | 3/2001 | Hotomi | 310/324 |
| 6,445,109 B2 | * | 9/2002 | Percin et al. | 310/324 |

FOREIGN PATENT DOCUMENTS

| | | | | |
|---|---|---|---|---|
| JP | 2-42184 | * | 2/1980 | 417/48 |
| JP | 2-140475 | * | 5/1980 | 417/413.2 |
| JP | 1-167475 | * | 7/1989 | 417/413.2 |
| JP | 6-198872 | * | 7/1994 | 347/68 |
| JP | 7-52381 | * | 2/1995 | B41J/2/045 |
| JP | 8-164608 | * | 6/1996 | B41J/2/045 |
| WO | WO 87/07218 | * | 12/1987 | B41J/3/04 |

OTHER PUBLICATIONS

IBM Technical Disclosure Bulletin, Oct. 1996, Self Contained Active Enhancement for Low Flowrate Liquid.*

"Electrochemical Detection of Localized Mixing Produced by Ultrasonic Flexural Waves," by T.R. Tsao, R.M. Moroney, B.A. Martin and R.M. White, Dec. 1991.

"Planar chips technology for miniaturization and integration of separation techniques into monitoring systems—Capillary electrophoresis on a chip," by Andreas Manz, D. Jed Harrison, Elisabeth M.J. Verpoorte, James C. Fettinger, Aran Paulus, Hans Ludi and H. Michael Widmer, Dec. 1992.

"Micromachining a Miniaturized Capillary Electrophoresis–Based Chemical Analysis System on a Chip," by D. Jed Harrison, Karl Fluri, Kurt Seiler, Zhonghui Fan, Carlo S. Effenhauser, Andreas Manz, Aug. 1994.

"Synchronized Cyclic Capillary Electrophoresis—A Novel Approach to Ion Separations in Solution," by Norbert Burggraf, Andreas Manz, Carlo S. Effenhauser, Elisabeth Verpoorte, Nico F. deRooij, and H. Michael Widmer, Oct. 1993.

(List continued on next page.)

*Primary Examiner*—Thomas M. Dougherty
(74) *Attorney, Agent, or Firm*—Fliesler Dubb Meyer & Lovejoy LLP (57) ABSTRACT

A microsized pump is set forth. It comprises a substrate which at least partially defines one or more walls of a longitudinally extending tunnel. The tunnel has a vibratable wall portion. A sonic energy generator is positioned in sonic energy transmitting relation to the vibratable wall portion. The sonic energy generator is adapted to generate elastic waves which travel along the longitudinal extension of the tunnel. The pump is useful for moving material along the tunnel whereby chemical and biological analysis and reactions can be carried out on a micro scale.

17 Claims, 10 Drawing Sheets

OTHER PUBLICATIONS

"Towards miniaturized electrophoresis and chemical analysis systems on silicon: an alternative to chemical sensors," by D. Jed Harrison and P.G. Glavina, Jun. 1991.

"Chemical Analysis and Electrophoresis Systems Integrated on Glass and Silicon Chips," by D. Jed Harrison, Andreas Manz, Kurt Seiler, Zhonghui Fan, Jun. 1991.

"Pneumatic Microsyringe for Use as an Injector in Open Tubular Liquid Chromatography and as a Dispenser in Microanalysis," by Robert T. Kennedy and James W. Jorgenson, Mar. 1988.

"A Gas Chromatographic Air Analyzer Fabricated on a Silicon Wafer," by Stephen C. Terry, John H. Jerman and James B. Angell, Dec. 1979.

"Ultrahigh Resolution Gas Chromatography—Contraints, Compromises and Prospects," by Walter Jennings, Dec. 1984.

"PCR in a Silicon Microstructure," by Peter Wilding, Mann A. Shoffner, and Larry J. Kricka, Sep. 1994.

"DNA Amplification with a Microfabricated Reaction Chamber," by M. Allen Northrup, Michael T. Ching, Richard M. White, and Robert T. Watson, Jun. 1973.

"Rapid Cycle DNA Amplification: Time and Temperature Optimization," by Carl T. Wittwer and David J. Garling, Dec. 1991.

"Normally Closed Microvalve and Micropump Fabricated on a Silicon Wafer," by Masayoshi Esashi, Suichi Shoji and Akira Nakano, Dec. 1988.

"An investigation of electrowetting–based microactuation," by Ed Colgate and Hirofumi Matsumoto, Jul. 1990.

"Acoustically Driven Flow in Flexural Plate Wave Devices: Theory and Experiment," by C.E. Bradley and R. M. White, Dec. 1994.

"Application of Micro Diaphragm Pumps in Microfluid Systems," by R. Zengerle, W. Geiger, M. Richter, J. Ulrich, S. Kluge, A. Richter, Dec. 1994.

"Microtransport induced by ultrasonic Lamb waves," by R.M. Moroney, R.M. White and R.T. Howe, Aug. 1991.

"Fluid Motion Produced by Ultrasonic Lamb Waves," by R.M. Moroney, R.M. White, and R.T. Howe, Dec. 1990.

"Liquid Streaming and Droplet Formation Caused by Leaky Rayleigh Waves," by S. Shiokawa, Y. Matsui and T. Ueda, Jul. 1989.

"Physical Acoustics—Principles and Methods," Properties of Polymers and Nonlinear Acoustics, vol. II, Part B, edited by Warren P. Mason, Dec. 1965.

"Study on SAW Streaming and its Application to Fluid Devices," by Showko Shiokawa, Yoshikazu Matsui and Toshihiko Ueda, Nov. 1989.

"Self–Assembled Monolayers in Separations," by Mary J. Wirth and Hafeez O. Fatuomba, LC–GC vol. 12 No. 3, Mar. 1994.

"Permeable Polysilicon Etch–Access Windows for Microshell Fabrication," by Kyle S. Lebouitz, Roger T. Howe and Albert P. Pisano, Jun. 1995.

"Digital micromirror device and its application to projection displays," by Jeffrey B. Sampsell, Nov. 1994.

"Current Status of the Digital Micromirror Device (DMD) for Projection Television Applications," by Larry J. Hornbeck, Dec. 1993.

"Status of the Mass Spectrograph on a Chip (MSOC)," Technical R&D Status Report, Jul. 1995–Dec. 1995.

* cited by examiner

FIG. 1

Piezo
FIG. 2

Re-entrant/cyclic chromatograph

MICROPUMP

CROSS-REFERENCE TO PROVISIONAL APPLICATION

This Patent Application claims the benefit of U.S. Provisional Application No. 60/009,665, filed Jan. 5, 1996.

FIELD OF THE INVENTION

The invention relates to micro sized pumps which transport chemicals on micro sized devices for chemical analysis on such devices and to micro sized chemical analysis systems utilizing such pumps. Typically, the pumps are formed on silicon chips.

BACKGROUND OF THE INVENTION

Advances in micromachining techniques have enabled the mass production of miniature and microscopic electromechanical components that perform a variety of functions. These components fall generally into two categories: sensors and actuators. Sensors can be made to monitor measurands such as pressure, acceleration, chemical-vapor concentrations, light intensity and magnetic fields. Actuators include pumps and valves for fluid manipulation, heated chambers to induce chemical reactions, moveable mirrors for optical displays and relay switches for high-frequency communications.

In addition to direct miniaturization and mass production, a feature of micromachining is that it enables the implementation of new types of technologies. With miniaturization, physical laws of scaling inherently favor certain technologies and phenomena over others. In some cases, technologies that can be made by micromachining work well on the microscopic scale but have no analogy or usefulness in the macroscopic domain (e.g., the electrostatic micromotor).

The ultimate power of microfabrication lies in the ability to integrate multiple components into complex microelectromechanical systems (MEMS) that have high functionality and performance, yet are small, easy to use and to produce, and inexpensive. An example of a complex microelectromechanical system is the digital micromirror display marketed by Texas Instruments, based on an array of a plurality of individually-addressable micromirrors.

One of the attributes of these systems is that they can be made fully self-contained and can be operated remotely without direct user intervention for sample handling or other tasks. Operation can be controlled with a combination of electronic hardware and software. The necessary drive electronics can be included on or off chip. In this way the ease of operation of these potentially powerful microinstruments is much simpler than most conventional analytical instruments, and more comparable to individual sensors.

In the area of instrumentation, microfabrication, micromachining, holds much promise for making small low-cost, fast-operating, portable, easy-to-operate systems for chemical analysis, clinical diagnostics and other applications. These microinstruments will rely on the integration of fluid-handling components.

Interest in microinstruments has been spurred by the need for improved chemical and biological analysis techniques in applications such as environmental remediation, chemical-warfare-agent detection and clinical diagnostics. For example, the DOE estimates that the superfund cleanup will require tens of millions of soil samples to be analyzed each year. The cost and manpower devoted to sample collection and analysis is exorbitant, and could be greatly reduced by using inexpensive, in-situ analyzers. However, the technology to make such analyzers is not available presently: existing sensors are very limited in their capabilities, and so-called portable analytical instruments are expensive and complicated to use.

Micromachining techniques of the nature disclosed in the present document allow the provision of analytical-instrument performance in microinstruments that are comparable in size, cost and ease-of-use to individual sensors. These same techniques can also be used to make disposable medical instruments such as DNA-based diagnostic tests, and miniature scientific instruments based on a number of technologies such as gas and liquid chromatography, electrophoresis, and flow-injection analysis. Several of these analysis techniques can be combined into a single chip to create very sophisticated systems that separate and analyze tiny samples without human intervention.

Essential for these microinstruments are suitable pump technologies to transport samples and reagents on the microscale. Many types of micromachined pumps have been developed recently. Most of these are discrete pumps, meaning that they operate by creating a pressure differential that drives fluids through the system in which they are functioning. The most common are silicon-based diaphragm pumps, which rely on electrostatic or thermo-pneumatic actuation to deflect a membrane that displaces fluid through one of two integrated check valves. Higher pump rates and higher pumping pressures have been achieved by actuating micromachined diaphragms with off-chip piezoelectric elements. These types of pumps are useful but have limitations. They are complicated to fabricate, subject to clogging, and pressure is generally limited by valve leakage. Discrete pump technologies also do not work well for moving fluids through microtunnels, i.e., through enclosed tunnels with cross-sectional dimensions of less than about 500 microns. This is because the pressure required to maintain a given flow rate increases extremely rapidly as the cross-sectional area of the tunnel is reduced.

Recently there has been much development of electroosmotic and electrophoretic pumps for liquid-based microinstruments. Electroosmosis is the movement of a liquid, under an applied electric field, in a fine tube or membrane. Electrophoresis is the movement of charged particles under an electric field in a liquid or gel. Electroosmosis and electrophoresis are very useful pumping mechanisms for liquid-based microinstruments. However, they do not work with gases, and are sensitive to the properties of the liquid such as conductivity and pH. Electroosmosis is also sensitive to the surface properties of the tunnel.

U.S. Pat. No. 5,006,749 to R. M. White describes methods for making an ultrasonic micromotor to move solids and briefly mentions the possibility of moving liquid droplets or streams. The method of this patent does not, however, describe a useful pump structure for moving fluids along an enclosed flow path, distributed pumping or chemical analysis instruments.

There is also recent work on fluid transport by acoustic streaming on a microscale. Acoustic streaming is steady fluid flow or pressure induced by high-intensity sound. It was first described by Faraday in 1831 and addressed theoretically by Rayleigh in 1884. Acoustic streaming fluid velocities are generally proportional to the square of the (mechanical) displacement of the driving source, and to the square of the acoustic displacement and velocity fields in the fluid. Acoustic streaming has been observed in fluids contacting vibrating cylinders, spheres, and plates.

Recently, steady-state pumping and localized stirring have been demonstrated with a micromachined flexural-plate-wave delay line. Pumping velocities as high as 30 mm/sec in air and 0.3 mm/sec in water have been observed.

The present inventors have shown as disclosed herein that a related structure can produce air flow rates of over 18 mm/sec in an enclosed tunnel 50 micrometers high, 500 micrometers wide and 8 mm long.

Acoustic streaming has also been generated with surface acoustic wave (SAWs). Shiokawa et al. have shown that water droplets can be ejected from the surface of a lithium niobate SAW delay line. This work does not, however, discuss structures that can move fluids in enclosed tunnels or in microsystems, or by distributed pumping.

Neither the White nor the Shiokawa et al. works describes a useful pump structure for moving fluids along an enclosed flow path, distributed pumping, or use with chemical-analysis instruments. Additionally, the flexural-wave structure has inherent limitations that prevent their use in forming a flexural-plate-wave pump or delay line from an enclosed narrow channel, that is, a channel with width less than about a wavelength. This is because in these configurations flexural-plate waves are generated via bimorph actuation using transducers that are uniform across the plate width. A composite plate is formed by laminating an actuation layer of a piezoelectric or electrostrictive material to one or more other layers. The center of flexure (neutral plane) of this plate is offset from the geometric center of the actuation layer. Flexural motion is produced when voltage is applied to the actuation layer, inducing a n in plane stress; since the neutral plane is offset from the center of the actuation layer, this stress causes the plate to flex. The entire area of the actuation layer under the applied voltage is driven into one in-plane stress state (compression or tension) causing the plate in that region to bend with one curvature (positive or negative). This mechanism works well when the plate width is large compared to the ultrasonic wavelength; however, when the plate is narrow compared to the wavelength and the plate edges are clamped (such as with the pump structure proposed wherein pumping is through a narrow tunnel) it is ineffective for producing flexural motion and flexural waves.

In the latter narrow geometry, the clamped plate edges have a large effect on the operation. For plate flexure to occur, the curvature of the plate at the midpoint between the edges must be opposite to that at the clamped edges. Bimorph construction with uniform transducers across the full width of the plate can not induce the opposite stress needed to produce these opposite curvatures, and thus is ineffective for producing flexural motion. Also, conversely, flexural motion and waves in this type of structure can not be detected effectively with a uniform transducer, because charge created piezoelectrically or electrostrictively near the edges of the plate will cancel that induced near the center, as these regions are in opposite states of curvature and stress. Furthermore, the boundaries make the generally less compliant to bending.

One of the first examples of a silicon-micromachined chemical-analysis system was a wafer-scale gas chromatograph developed by Terry et al. at Stanford University. The design was based on a conventional gas chromatograph (GC), which has five main components: (1) separation column, (2) detector, (3) sample injector, (4) column heater, and (5) bottled pressurized carrier gas. The pressurized carrier gas is attached to the inlet of the column and used to force gases through the column and into the detector on the end of the column. The sample injector typically employs a multiport valve between the bottled carrier gas and column to introduce a plug of sample gas into the carrier gas at the column inlet, which is under pressure. The sample is generally a mixture of known or unknown chemicals in different concentrations. After the sample plug is injected, it travels down the column with the carrier gas, and interacts with a coating on the interior walls of the column termed the stationary phase. This interaction causes the chemical components of the sample to be retained differentially, so that they become spatially separated as they travel down the column. The detector is generally a non-specific sensor that tells the presence or absence of a chemical. As the chemical components pass the detector, it outputs a series of peaks called a chromatogram. An individual chemical component is identified by its retention time. The column heater is needed stabilize column temperature so that retention times are predictable; additionally, it can be used to speed analysis times by temperature ramping.

Component identification is chromatography can also be aided by using multiple detectors that respond differently to a given set of chemicals. For example, using both a photo-ionization detector and a SAW sensor will yield more information than either detector alone. The mass spectrometer is another powerful analysis system that is used both alone and as a chromatographic detector; it separates and identifies chemicals by atomic mass. Microsized and microfabricated mass spectrometers are currently under development by Carl Friedhoff, et al at Northrup Grumman Corporation.

In conventional GCs, these components are all macroscopic in size; for example, the column is typically a coiled, fused-silica capillary around 10 meters in length. The resulting GC systems are bench-top-sized or larger with power requirements of hundreds or thousands of Watts.

Terry miniaturized a conventional GC by micromachining: the column was fabricated on a silicon wafer, to which individual silicon valves were attached for sample injection, and a thermal-conductivity detector for sample detection. This demonstrated that all of these components can be miniaturized by micromachining, with the exception of the bottled carrier gas.

Though innovative, the Terry GC did not perform as well as expected. The silicon-micromachined column had a non-round cross section unlike conventional fused-silica capillary columns and could not be coated evenly with a stationary phase, leading to poor performance or efficiency and resolution. Efficiency refers to the resolution of separation that can be achieved with a given length of column: A column with high efficiency separates and resolves chemicals in a shorter distance than a column with lower efficiency. The design did not provide any inherent advantages over a conventional GC in terms of manufacturing costs or performance, and the advantage of size reduction was negated by the need for bottled carrier gas. A company founded on this technology now produces portable gas chromatographs that use a few micromachined parts but still employ conventional fused-silica capillary columns and weigh several pounds.

Currently there is rapid development of liquid-phase microinstruments based on electroosmotic pumping. This technology has been used to create chip-based capillary-electrophoresis units with on-chip sample injection. Recently, a cyclic electrophoresis unit has been demonstrated. This demonstrates how micromachining can be used to produce devices that are not possible using conventional (i.e., fused-silica capillary) techniques.

SUMMARY OF THE INVENTION

In accordance with an embodiment of the invention a micro sized pump is set forth. It comprises a substrate which at least partially defines one or more walls of a longitudinally extending tunnel. The tunnel has a vibratable wall portion. An ultrasonic energy generator is positioned in ultrasonic energy transmitting relation to the vibratable wall portion. The ultrasonic energy generator is adapted to generate elastic waves which travel along the longitudinal extension of the tunnel. The pump is useful for moving material along the tunnel whereby chemical and biological analysis can be carried out on a micro scale.

Another embodiment of the invention is a chromatographic column comprising the pump as set forth above with walls of the tunnel being coated with a stationary phase.

Yet another embodiment of the invention is a chromatograph which includes the coated tunnel, a sample injector and one or more detectors; where appropriate a column heater is also provided.

Still another embodiment of the invention is an analysis system comprising the pump as set forth above in combination with any desired chemical analysis station with the pump being used to deliver a sample to be analyzed to the analysis station.

Attached hereto and incorporated herein by reference in its entirety is priority Provisional Patent Application Serial No. 60/009,665 filed Jan. 5, 1996 which includes still other embodiments of the invention.

The present invention uses ultrasonic waves to move gases, liquids and particulate solids within and along a tunnel by the physical phenomenon of acoustic streaming. Elastic waves traveling along the interface of a solid and a fluid produce intense sound in the fluid, causing it to move with some component of motion along the interface. The pump is formed with a tunnel that has elastic waves propagating along its wall thereby moving fluids longitudinally along the tunnel. The structure also has transducers which are used to generate the elastic waves.

This acoustic streaming pump is novel and has distinct advantages over other types of pumps, thereby enabling many applications in miniature/micro fluidic systems. In contrast to discrete pumps (such as diaphragm pumps) the mechanism that induces fluid motion (elastic wave motion) is distributed over the length of a flow tunnel. Furthermore, the elastic waves act on the fluid very close to the interface with the wall. The result is that the pump moves fluids down long shallow and narrow tunnels without incurring the pressure limitations of discrete pumps. The fabrication of this pump is also simple compared to most micropumps. It has no moving parts that are prone to mechanical failure. It is also distinctly different from the ultrasonic transport technologies described by White et al and the work of Shiokawa et al, which only move fluids on an open surface, or recirculate them in a well.

The present invention is also a significant departure from prior art as it describes structures and transducers that are effective for forming enclosed, narrow-channel acoustic pumps and sensors based on flexural plate waves as well as other types of ultrasonic waves.

The invention also includes microinstruments based on the pump.

BRIEF DESCRIPTION OF THE DRAWINGS

The invention will be better understood by reference to the figures of the drawings wherein.

BEST MODE FOR CARRYING OUT INVENTION

A system is described that improves the performance of an individual sensor by reducing drift of its output signal caused by undesirable interferences such as temperature and aging. A pump draws an analyte, generally a gas, past a concentration modulator to a sensor. The user programs the concentration modulator to vary the concentration of analyte reaching the sensor. The sensor system is otherwise unaffected by the concentration monitor. The sensor output signal then varies in synchrony with the concentration modulator when the analyte is present; the sensor response due to the analyte can thus be separated from uncorrelated drift.

The pump is used to make a miniature, simple, high-performance GC that is not possible with conventional components. A micromachined separation column is made with the pump distributed along a desired portion of its length. The pumped column draws the carrier gas and sample through it, so that pressurized carrier gas is not needed to induce flow. Since the system is not under pressure, valves are not needed for injecting the sample. Sample collection and injection can be performed with sorptive materials on a temperature-controllable platform near the column inlet. Detection can be achieved with one or more sensors, positioned near the column outlet, that are appropriate for the chemicals of interest. A further simplification of the system is achieved by using detectors that can operate in air rather than just in a specific type of carrier gas (such as helium). Then ambient air can be used for the carrier gas, eliminating the bottled, pressurized carrier gas altogether. The entire system (sample injector, pumped separation column and detectors) can be integrated on single chip of area less than about 1-cm$^2$, with the appropriate choice of miniature detectors. A column heater can also be included in this area, if appropriate. Electronics to drive, control and interrogate the system can be included on or off the chip.

Generally, the GC system may operate as follows: The ultrasonically pumped column draws sample air through the sample collector and column for a specified period of time; the temperature-controlled platform is heated quickly to desorb and inject a plug of the collected sample into the column; the sample plug is drawn down the column by the pump and separates into its different chemical components, which are detected by the detectors. The temperature of the optional column heater can be set to a specific temperature or varied during operation.

One type of detector that may be used is an ultrasonic sensor, which uses the same basic technology as the ultrasonic pump. An ultrasonic delay line is coated with a chemically sensitive film; when chemicals are present, they interact with the film and change its mass, and with it the ultrasonic wave velocity. The velocity change is measured electronically and correlated with chemical concentration.

In another implementation, an ultrasonic pump separate from that of the column can be used to draw sample air through the sample collector. The invention may also include filters to prevent particles and aerosols from clogging or otherwise adversely affecting the system. A denuder may also be included to scrub the carrier gas.

Other benefits accrue from using the ultrasonically pumped separation column. The efficiency or effectiveness with which a column separates chemicals increases as the cross section of the separation column is reduced. In conventional GCs there is an effective minimum column width of several hundred micrometers, which is dictated by the pressure required to force carrier gas through the column at a given rate, and by the flow requirements (including dead volume) of sample injectors and detectors. The use of high pressure increases the cost and complexity of the associated equipment, and causes "band broadening", which reduces resolution. By employing ultrasonic pumping, the invention allows columns of arbitrarily small cross section to be used, without the limitations of pressure driven flow. Higher flow velocities can be used to gain even higher efficiency and faster analysis. The high-efficiency columns enabled by the distributed pumping can also be shorter to obtain the same resolution, aiding further in miniaturization.

Furthermore, the narrower columns allow different types of stationary phase materials to be employed. As the column cross section is decreased, the stationary-phase thickness required to achieve a desired efficiency also decreases, as does analysis time. Column cross sections can potentially be reduced enough to permit single-molecule layers, such as self-assembled monolayers (SAMs), to be used for the stationary phase. SAMs are organic molecules that can be grown in highly ordered, single layers on surfaces. J. Wirth and H. O. Fatunmbi, LG-GC, Volume 12, No. 3, pp. 222–228, March 1994, demonstrates the use of a SAM film as the stationary phase in a liquid chromatograph. SAMs offer the potential to obtain uniform, high-quality stationary phase coatings on columns of arbitrary cross-sectional shape and dimensions.

A chemical or biological reaction system can be constructed utilizing a pump as set forth herein. Such a system can comprise one or more of the pumps as described in detail below in combination with a reaction region adjacent the substrate. The reaction region is connected to receive a reaction sample having one or more reactants which are pumped there via one or more tunnel(s) and to carry forth a reaction to form a reacted sample. The system can include an additional reaction region, the additional reaction region being connected to receive the reacted sample pumped via a tunnel and to carry forth an additional reaction to thereby form a further reacted sample. The additional reaction region can be connected to receive one or more additional reactants for reaction with the reacted sample to thereby form the further reacted sample.

Figure 1:
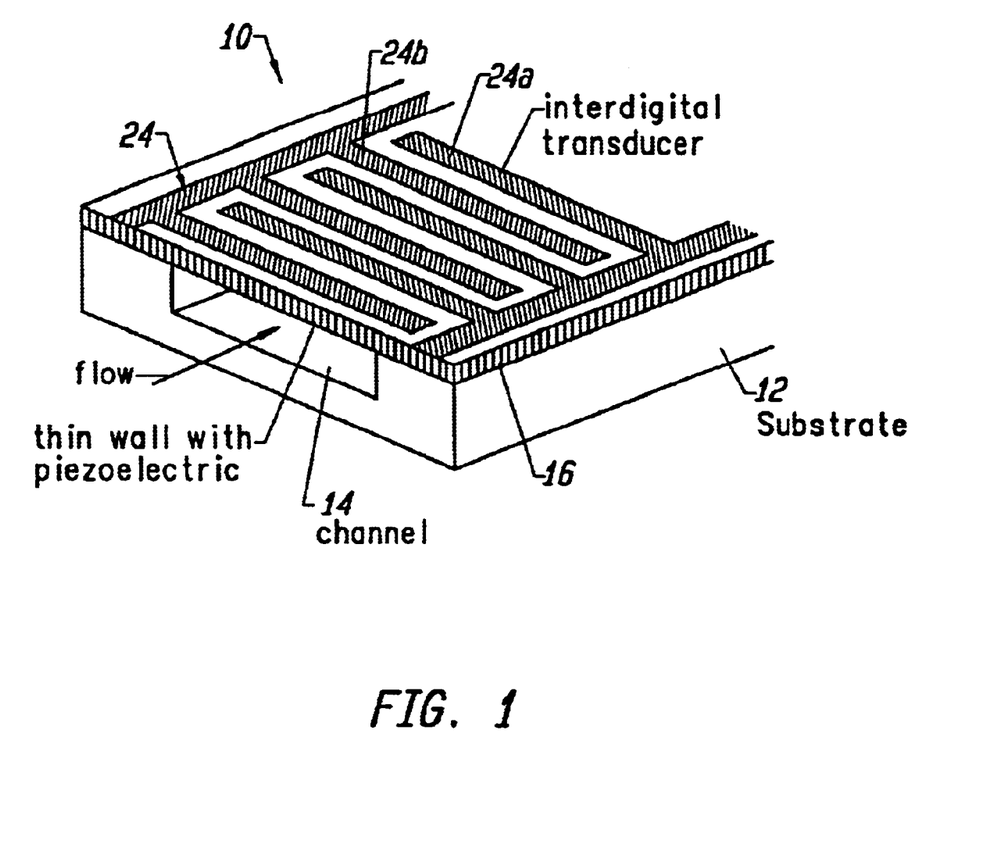
FIG. 1 illustrates, in isometric view, a pumping structure in accordance with an embodiment of the invention which provides ultrasonic pumping along a tunnel on a micromachined substrate.

FIG. 1 shows a preferred embodiment of a pump structure 10 in accordance with an embodiment of the invention. A substrate 12, made of a material, such as, for example, silicon, fused silica or quartz, has a longitudinally extending tunnel 14 formed in it. A vibratable member, in the embodiment of FIG. 2 a thin 16, covers the tunnel 14. The material of the substrate 12 is not at all critical and the invention can be applied using any desired substrate material so long as it has sufficient structural integrity.

The term plate, as used herein, is a solid media with two surfaces that are free or bordered by mechanically compliant media. The plate may be clamped so that it is of limited subject to stress, such as in-plane tension or compression.

Plate waves, as defined herein, are elastic waves that propagate in plates, as defined herein. These include modes akin to Lamb waves, which have particle motions both longitudinal and transverse to wave propagation, the transverse motion being perpendicular to the plate surfaces or plane of the plate. Also included are shear horizontal plate waves, in which displacements are transverse to the direction of propagation and in the plane of the plate. Strictly speaking, Lamb modes can only exist in plates that have both surfaces free, are of infinite extent in the two dimensions in the plane of the plate, and are stress free. The structures presented herein use plates that deviate from this structure significantly; therefore the elastic waves that can be supported are not strictly Lamb or shear-horizontal plate modes. For example, the lowest-order antisymmetric Lamb mode (A0 mode) in a free plate is sometimes termed the "flexural plate wave". Narrow-plate structures are disclosed herein that can support flexural waves that differ from the A0 mode because the particle motion contains transverse components that are in the plane of the plate. Furthermore, the propagation properties (e.g., velocity and frequency) of this flexural wave are affected strongly by the finite plate width and the clamping conditions and can not be predicted/ derived accurately using the Rayleigh-Lamb frequency equation, which describes Lamb-wave propagation.

Figure 2:
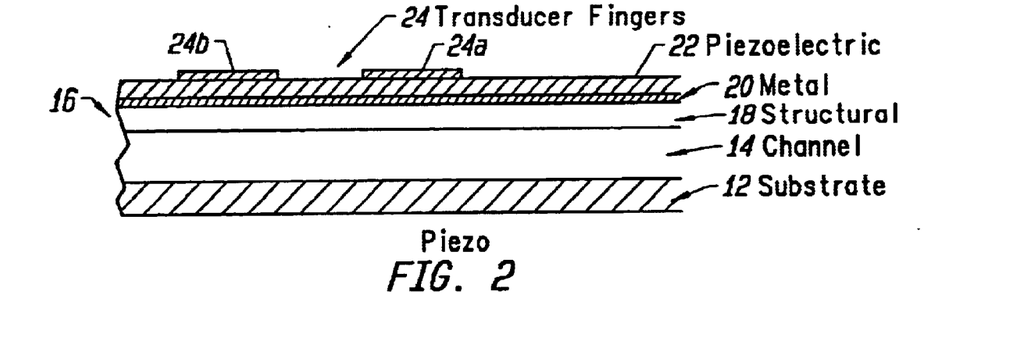
FIG. 2 illustrates, in side section partial view, a piezoelectric embodiment of FIG. 1.

Referring to FIG. 2, the thin plate 16 can suitably be made of a structural layer 18, an electronically conducting layer 20 and a piezoelectric material layer 22. For example, the layers can be silicon dioxide, aluminum and zinc oxide, respectively. While specific materials are set forth it should be recognized that the invention is not limited to the use of these materials and that substantially any structural, electronically conducting and piezoelectric materials may be used in their place. By way of example and without limitation some other useful piezoelectric materials are aluminum nitride, lead zirconate titanate, barium titanate and lithium niobate. Provision of the electrically conducting layer 20 works well and is preferred but such a layer is not a necessity.

A conductive transducer 24, suitably made of any conductive material such as a metal, in the form of a first plurality of interdigited fingers 24a and a second plurality of interdigited fingers 24b, sits atop and is in elastic wave generating contact with the piezoelectric layer 22. The fingers are arranged substantially parallel relative to one another and extend along the longitudinal extension of the tunnel 14. To operate this structure as a pump, an alternating voltage is applied between the layer 20 and the interdigited fingers 24a, 24b of the conductive transducer 24. This creates strain in the piezoelectric layer 22 and generates ultrasonic waves that travel longitudinally down the tunnel 14 in the substrate 12. Gases or liquids in the tunnel 14 move down the tunnel 14. For most efficient operation, an alternating voltage is applied between the fingers 24a and the conducting layer 20 at 180° out of phase with the voltage applied between the fingers 24b and the conducting layer 20. The frequency is adjusted such that the elastic wavelength is equal to P. This results in a maximized acoustic wave of the same frequency as the alternating voltage. Less efficient but useful operation is practical when these parameters are deviated from. Generally, the distance between adjacent pairs of fingers must be no more than the distance the elastic waves will sustain themselves along the tunnel.

Single-phase transducers may also be used, wherein a single set of electrodes at the same voltage is used to generate or detect waves. Single-phase transducers are usually less efficient than multiple-phase transducers.

Figure 3:
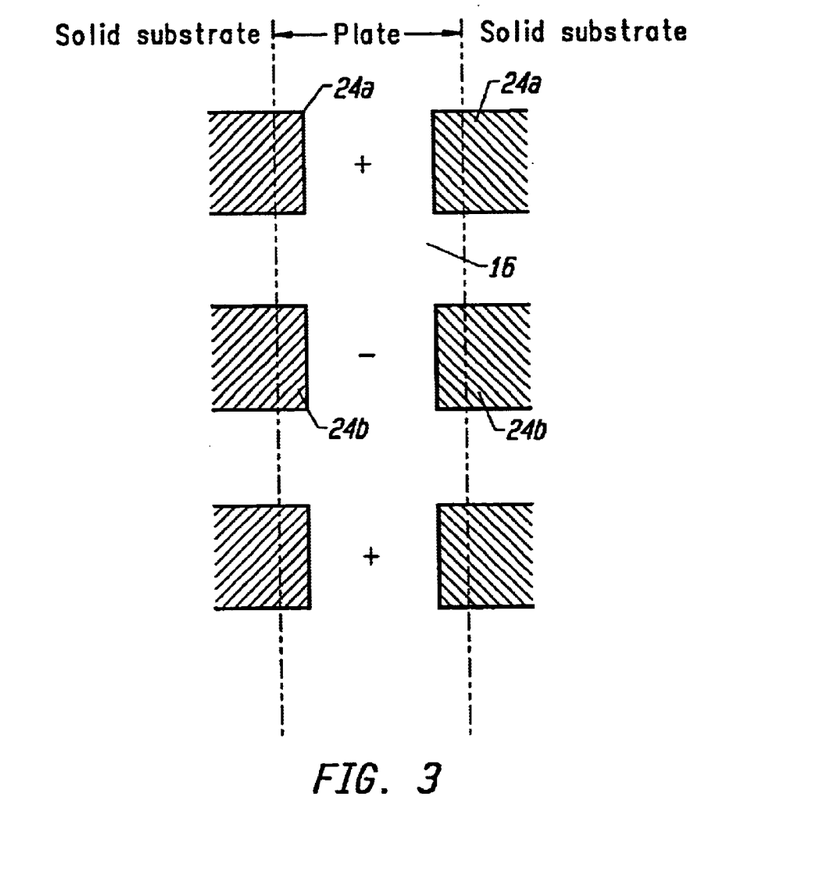
FIG. 3 shows another preferred piezoelectric embodiment that uses a new transducer design that is more efficient than a uniform transducer for generating and detecting flexural motion and flexural waves in the walls of narrow channels.

FIG. 3 shows electrodes 24a, 24b in top view with the electrodes extending part way across the plate 16 from its periphery.

Figure 4:
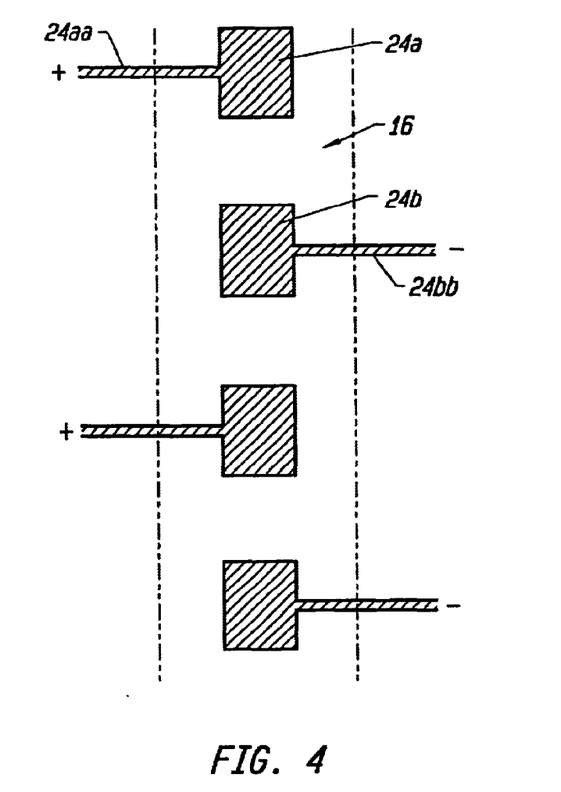
FIG. 4 shows another preferred piezoelectric embodiment that uses a second new transducer design that is more efficient than a uniform transducer for generating and detecting flexural motion and flexural waves in the walls of narrow channels.

FIG. 4 shows electrodes 24a, 24b in top view which extend laterally onto the center portion of the top of the plate 16 with the contacts 24aa, 24bb being as small as possible so that the electrodes are centered.

Figure 5:
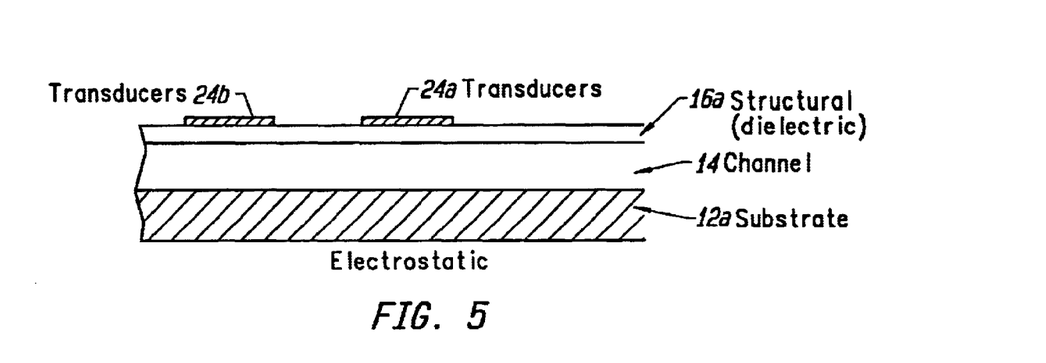
FIG. 5 illustrates, in side sectional section partial view, an electrostatic embodiment of FIG. 1.

FIG. 5 shows a second embodiment of the pump 10, using electrostatic actuation to generate wave motion. In the embodiment of FIG. 5 the substrate 12a must be conductive (as illustrated) or must have a conducting layer (not illustrated) on it. The tunnel 14 is closed at its top by a thin plate 16a which forms a wall of the tunnel 14 and is made of a dielectric such as, for example, silicon, fused silica, quartz or silicon nitride. The materials specified are merely illustrative. Substantially any nonconductor which has the requisite structural integrity can be used. Thus, for example, plastics can be used. A set of interdigited transducers 24a, 24b, made of a conductive material, such as a metal, is located atop the thin plate 16a. To operate this structure, an alternating voltage is applied between the transducers 24a, 24b and the substrate 12a. Electrostatic attraction between the transducers 24a, 24b and the substrate 12a creates strain in the thin plate 16a, generating ultrasonic waves that travel down the tunnel 14. This structure is especially useful for generating flexural waves, because electrostatic force bends the plate directly out of plane. This implementation will work best when the tunnel width is less than the ultrasonic wavelength.

This is because local bending under the transducers is needed to generate flexural waves, which is difficult to achieve with a wide structure. The transducers generate a net force on the plate that tends to pull the entire plate toward the substrate. If the plate is wide compared to the transducer period P, the entire plate deflects, and there is very little local bending under the transducers. In a narrow structure (plate width less than P) the clamped plate edges counter the net plate force and prevent the entire plate from bending, but do allow local bending under the transducers.

Figure 6:
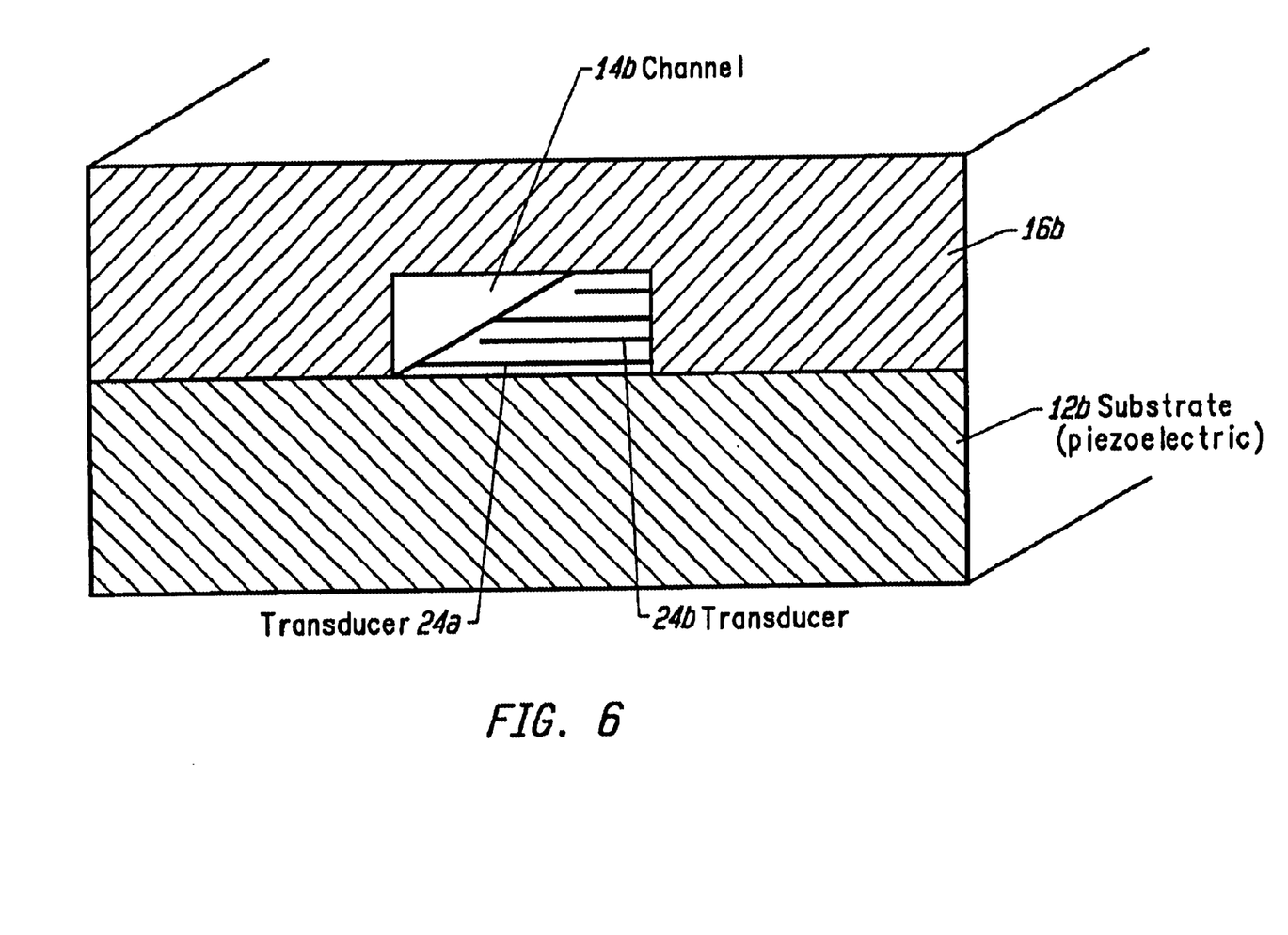
FIG. 6 illustrates, in isometric end section view, an embodiment as in FIG. 5 which utilizes an SAW-based pump.

FIG. 6 shows yet another preferred embodiment of the pump 10 that employs surface acoustic waves. In the embodiment of FIG. 4 the substrate 12b is made of, or has on the portion of it which forms a portion of the wall of the tunnel 14b, a piezoelectric material. On the substrate 12b, within the tunnel 14b, are interdigited transducers 24a, 24b. Atop the substrate 12b is a tunnel plate 16b in which the tunnel 14b is formed. The tunnel plate 16b is bonded to the substrate 12b to form the enclosed tunnel 14b with the pluralities of interdigited fingers 24a, 24b extending longitudinally along a desired portion of the length of the tunnel 14b. This embodiment is much like the FIG. 2 embodiment and operates similarly. The difference is that of geometry, and of the type of waves that are generated and induce the pumping. Substrate 12B is generally about the same thickness or thicker than the ultrasonic wavelength. Therefore surface acoustic waves are generated.

Unidirectional designs and transducers

In order to generate streaming flows and pumping, it is essential that propagating elastic (ultrasonic) waves are used, rather than standing waves. This means that the structure has to be capable of generating elastic waves that travel in a single direction along the tunnel. This so-called unidirectional design can be accomplished in different ways. One way is to use transducers that are specifically designed to be unidirectional. Many of these are reported in the literature. Another way is to use a bi-directional transducer (which may be simpler to fabricate and operate than a unidirectional design) in conjunction with an ultrasonic-wave reflector or absorber in the path of the ultrasonic-wave. An ultrasonic-wave reflector will generally be positioned in spacial relation to a transducer such that waves incident upon it in the non-preferred direction reflect and propagate in phase with waves emitted from the transducer in the preferred direction. An ultrasonic-wave absorber will simply damp and absorb the waves propagating in non-preferred directions to leave the wave traveling in the preferred direction. In all of the figures, bi-directional transducers are shown for ease of depiction/description. However, it is intended that for pump operation, the actual structure will be unidirectional, whether it be by transducer design alone, or by a combination of transducer design with ultrasonic reflectors and absorbers.

Reflectors may be made from any structure that causes a large impedance discontinuity in the ultrasonic path. If the material is mechanically rigid and thick enough, it presents a large impedance mismatch and acts as a wave reflector. A reflector can also be formed form a slot part or all of the way through the plate (or substrate for SAWs). A mechanically lossy or viscous material may be used to form an elastic wave absorber.

Ultrasonic-absorbing sections can also be used to terminate sections of the propagation path.

Electrostatic drive separate from tunnel

Figure 6A:
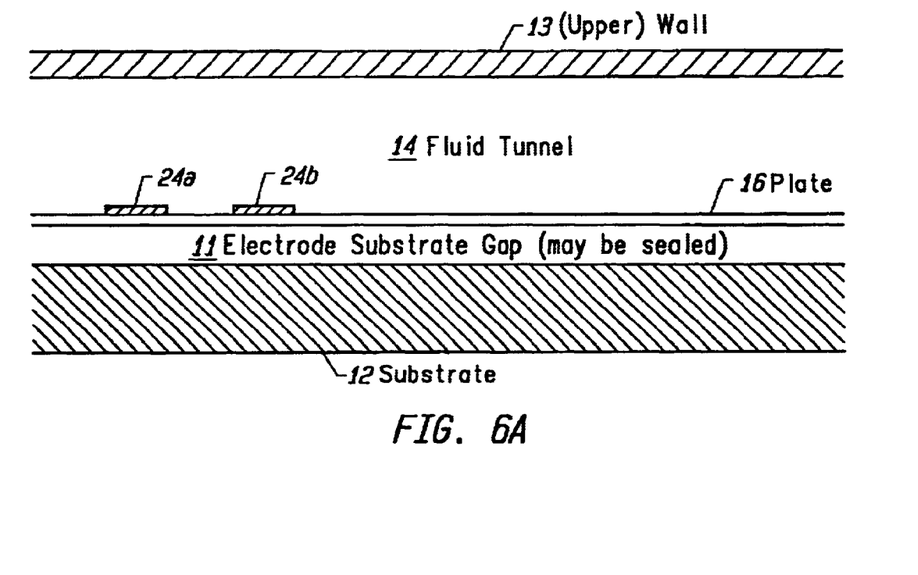

FIG. 6a shows another embodiment of the pump invention, where a tunnel 14 is built above the substrate 12. The ultrasonically driven plate 16 forms the lower wall of the fluid tunnel 14 shown in FIG. 6a with the tunnel being covered by an upper wall 13. This configuration can be advantageous because the ultrasonic drive portion is separate from the fluid tunnel 14, giving more design freedom for the individual components. For example, height of the fluid tunnel 14 height can be designed arbitrarily large to accommodate different fluids and flow rates, while a plate-to-substrate spacing 11 can be small (of order 0.1 to 10 microns) so that large electric fields can be generated with low voltages. The bending force and displacement (deflection) experienced by the plate 16 due to the electric field are proportional to the square of the electric field strength, which is equal to the applied voltage divided by the electrode-substrate spacing. Therefore, larger-amplitude waves and more efficient operation can be obtained for a given voltage by using smaller electrode-substrate spacing.

Figure 6B:
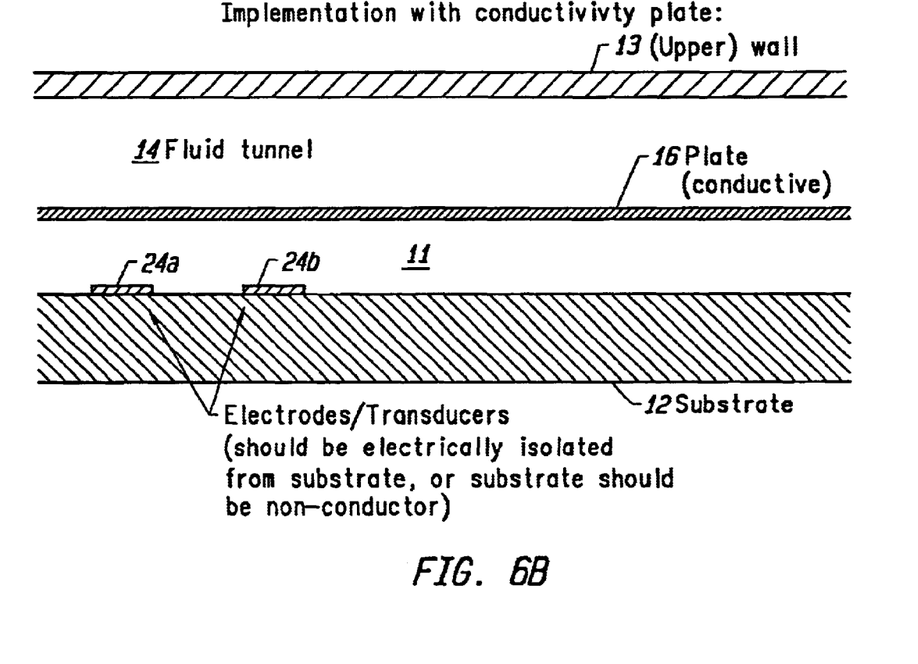

The electrodes 24a, 24b can also be located on the substrate 12 as shown in FIG. 6b, in which case the plate 16 must be conductive, or have a conductive material on it so that voltage can be applied between electrodes and plate.

Furthermore, the medium between the electrodes 24a, 24b and the substrate 12 can be sealed into the plate-to-electrode volume, and can be different than that in the fluid tunnel 14. The medium should be a dielectric, and should have low mechanical stiffness, so that it is compliant to compression as the plate above it bends. In the preferred embodiment this medium is a gas, a gas at reduced pressure or even vacuum. Wave generation and propagation may be optimized by using a low-pressure gas medium in the plate-substrate space 11 (rather than a liquid, solid or gas at higher pressure, such as atmospheric pressure). This is because any medium in this space will impede the plate motion with both elastic and viscous-damping components; with a gas these components are small to begin with and decrease in magnitude toward zero as the gas pressure is decreased toward zero. Furthermore, due to the Paschen effect—an increase in voltage and electric field needed to breakdown gas between electrodes as the electrode spacing decreases—larger electric fields can be sustained across a thin gas layer than across a correspondingly thin solid or liquid dielectric.

Also, large electric fields, typically on the order of $10^6$ V/cm, are typically needed to generate force sufficient to bend the tunnel wall, in this case the plate 16. The large fields are primarily confined in the plate-substrate gap 11 external to the tunnel 14, and will have little or no effect on the materials and processes inside the fluid tunnel 14. This may be very advantageous when a liquid or conducting liquid is present inside the fluid tunnel.

External electrostatic drive

Figure 6C:
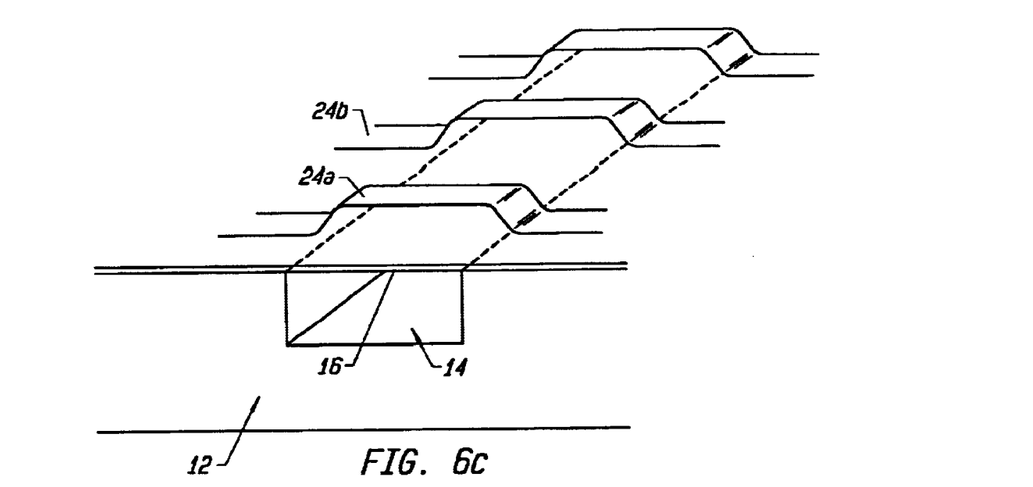

FIG. 6c shows another embodiment of the pump invention, whereby ultrasonic wave motion is generated by a transducer composed of electrodes 24a, 24b separated from a plate 16 which serves as the upper wall of the tunnel 14. Alternating voltage is applied between electrodes 24a, 24b and the tunnel plate 16, generating an attractive force between these two that causes the plate 16 to bend, thereby generating flexural waves. The plate must be conductive or have a conductive layer on it. A single set of electrodes, for example, the electrodes 24a without the electrodes 24b, may be used in which case they will act as a single phase transducer. The use of multiple phases, e.g., the two-phase system described, is preferable as this provides efficiency and versatility for making the waves unidirectional.

This configuration is advantageous because the gap height between electrodes 24a, 24b and the channel plate 16 can be changed independently of the tunnel depth. Also, the large electric fields needed to generate force sufficient to bend the plate terminate at the plate because it is conductive; therefore these fields are completely external to the fluid tunnel 14 and will not affect the materials and processes inside the tunnel 14. This may be advantageous when a liquid or conducting liquid is present inside the tunnel.

The (electrostatic) transducer designs shown) can also be used for receiving or detecting ultrasonic waves. Ultrasonic waves in the plate 16 may pass below the transducer electrodes 24a, 24b and change the gap spacing. This change in gap spacing can be detected electronically to sense the waves and their properties. For example, the capacitance between the electrodes 24a, 24b and the plate 16 is inversely proportional to the gap height; therefore, capacitance changes can be used to measure wave amplitude and frequency. Capacitance can be measured in different ways; one method is to apply a voltage between the electrodes 24a, 24b and the plate, and sense the current traveling to and from the resulting capacitor. Multiple transducers can be placed along a delay line to generate and detect waves.

High-pressure/vacuum pump

Figure 6D:
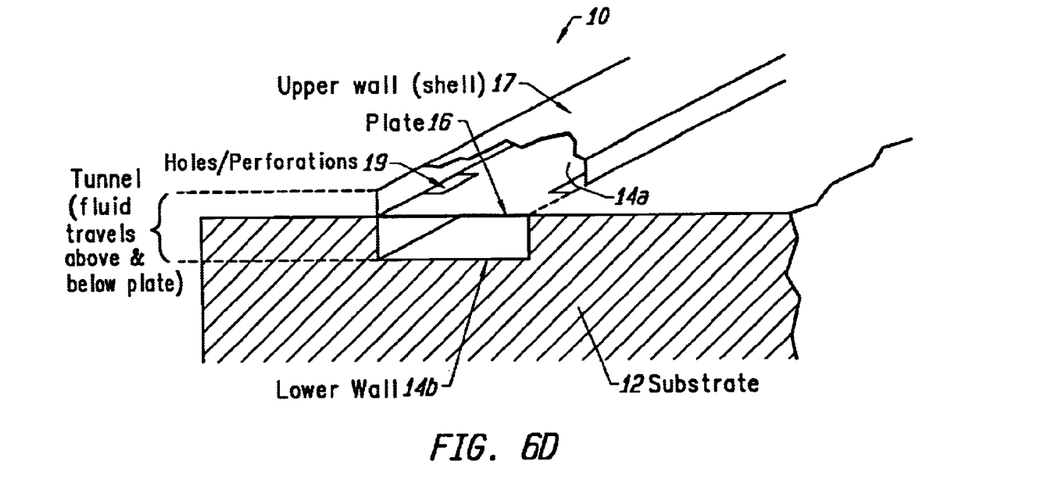
Figure 6E:
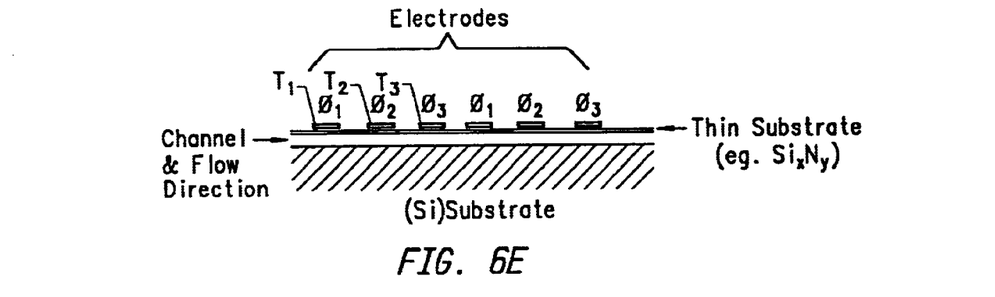

A structure as shown in FIG. 6d may be used to pump fluids against an external differential pressure and to create a large pressure differential between its ends. A tunnel can be formed in two parts, 14a and 14b to serve as a fluid conduit. The tunnel part 14a is formed from a top shell portion 17 and the substrate 12. A plate 16 serves as the bottom of the tunnel part 14a and as the top of the tunnel part 14b. The plate 16 supports ultrasonic waves that transport fluid down the length of the tunnel. The plate 16 may have perforations 19 in it to allow the pressure to equilibrate across it, such that plate 16 does not experience differential fluid pressure across it that would cause it to deflect. Transducers (electrostatic, piezoelectric, magnetic, etc) are used to generate traveling elastic waves in the plate 16 as with previously described embodiments.

In operation, the overall tunnel is narrow and shallow enough to present a high impedance to fluid flow that would be caused by differential pressure applied between the ends of the tunnel. Ultrasonic waves in the plate 16 form a distributed pump that transports fluid down the length of the tunnel more effectively than externally applied pressure. Thus, the pump 10 can transport fluids even in the presence of, and working against, an externally applied pressure. Conversely, this distributed pump 10 may used to create a differential pressure by pumping fluids to or from a sealed or partially-sealed volume.

An advantage of this structure is that the shell 17 and the substrate 12 that form the walls of the overall tunnel can be designed arbitrarily thick, stiff and strong enough to sustain a high pressure differential (for example, one atmosphere or greater) between the inside and outside of the tunnel. The plate 16 never experiences differential fluid pressure, and so can be built as thin as necessary to be compliant to plate-wave generation by the transducers. (Flexural rigidity of a plate—the resistance to bending—decreases as the plate thickness decreases. Therefore, the force required to generate flexural waves of a given amplitude decreases as the plate thickness decreases.) The pump efficiency and ability to move fluids against an external pressure can be adjusted by design. The tunnel can be made longer, or its cross section decreased, in order to increase impedance to external flow. Decreasing the tunnel height (distance between inside of shell 17 and substrate 12) increases the average pumping velocity across the channel. One application is as a vacuum pump, where the invention is attached to a volume and evacuates it until the pressure is below the ambient.

Processing

The structures discussed herein may be fabricated in a number of ways which generally rely on integrated-circuit and other microfabrication techniques such as photolithography, thin-film deposition, wet-chemical and plasma etching and wafer bonding. A preferred method to form a tunnel 14 sealed by a thin plate wall 16 is to use wafer bonding and etch-back techniques. Channels or grooves are made in a first wafer or substrate using standard photolithographic techniques to define the groove, and then etching into the substrate with wet chemicals or a plasma. A second wafer is coated with a thin layer of structural material that will act as the channel wall, such as silicon nitride or silicon dioxide. (Silicon nitride can be deposited by low-pressure chemical-vapor deposition (LPCVD) for example, or silicon dioxide may be grown thermally with standard IC processes.) The wafers are then bonded using one of several bonding techniques, such as fusion or anodic bonding. After bonding, the second wafer is etched away, stopping on the structural layer. The etching can be performed with a combination of mechanical grinding, chemical-mechanical polishing (CMP) and chemical etching. Alternately, the material of the second wafer (such as silicon) can be used as the structural plate material, by using CMP to etch the second wafer sufficiently thin (in this case, deposition of a structural material is not needed). This leaves the thin-walled tunnel structure on the first wafer. Next, the appropriate electrodes are deposited. Metal may be deposited by sputtering or evaporation. Piezoelectric materials may be deposited by sputtering, sol-gel, CVD or metal-organic deposition techniques. All layers can be patterned with standard photolithographic techniques and wet-chemical or dry (plasma) etching or lift-off.

Another technique for making thin-walled tunnels is to use so-called permeable poly (see Lebouitz et al, Permeable polysilicon etch-access windows for microshell fabrication, Proc. 8th Intern. Conf. on Solid State Sensors and Actuators and Eurosensors IX, Stockholm, Sweden, Jun. 25–29, 1995 which is incorporated herein by reference). A sacrificial layer such as PSG (phosphosilicate glass) is deposited on a substrate or wafer and patterned into channel shape. A thin layer of polysilicon is deposited under conditions such that it is permeable to wet chemicals. The PSG layer is then etched through the permeable poly using hydrofluoric acid. Next, the HF is removed by soaking in deionized (DI) water, and the DI water removed by heating or by supercritical fluid extraction. This leaves a shell of polysilicon. Further processing can then be performed, such as deposition of materials to seal the shell, and subsequent metal and piezoelectric deposition, photolithography and etching.

Thin walled tunnels can also be formed using xenon difluoride processing techniques where a sacrificial layer (e.g., polysilicon) is etched from underneath a shell of structural material such as silicon nitride.

As yet another alternative, the substrate can be a plastic and the tunnels, etc. can be formed by a molding step.

The stationary phase will usually, but not always, be applied in the liquid phase, requiring that solvents be removed at a later stage. Solvent extraction may be difficult using conventional techniques with these long, fine, thin-walled tunnels, and may be aided/effected by supercritical fluid extraction.

For example, a miniature DNA-diagnostic or analysis system may be built using the polymerase chain reaction (PCR)—a technique that replicates (or "amplifies") DNA very rapidly. PCR is used to create a "significant" sample of DNA from an original sample that was too small to analyze. PCR targets a given section of the original DNA, and can yield an end sample that contains millions or billions of copies of the base sequence contained in this section of original DNA. The end sample can then be analyzed in various ways. For example, simple detection schemes can be performed to determine the presence or absence of products; separation of the end products can be performed to determine contamination. PCR requires mixing/combining a DNA sample with other compounds such as primers and XXX, and then going through a repetitive heating sequence.

In another embodiment, a peristaltic pump may be formed using multi-phase transducers with three phases or more. FIG. 6f electrodes T1, T2 and T3 are driven with voltages at phases $\phi 1$, $\phi 2$ and $\phi 3$ respectively. These voltages are phased such that the plate displacement that constricts the tunnel is induced under the electrodes and moves in a single direction. The movement of the constrictions cause fluid pumping by peristaltic action. The velocity at which the constrictions move is determined by the frequency and phasing of the applied voltage, and does not depend on the elastic wave velocity.

Figure 7:
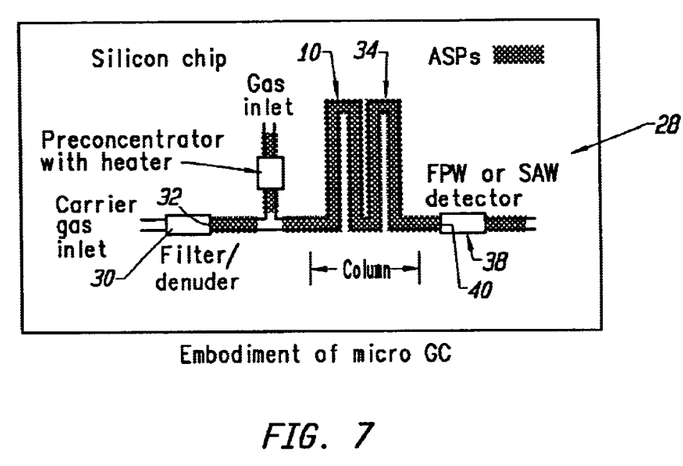
FIG. 7 illustrates, schematically, a microsized gas chromatograph used with a pumping structure in accordance with one or more embodiments of the invention.
Figure 8:
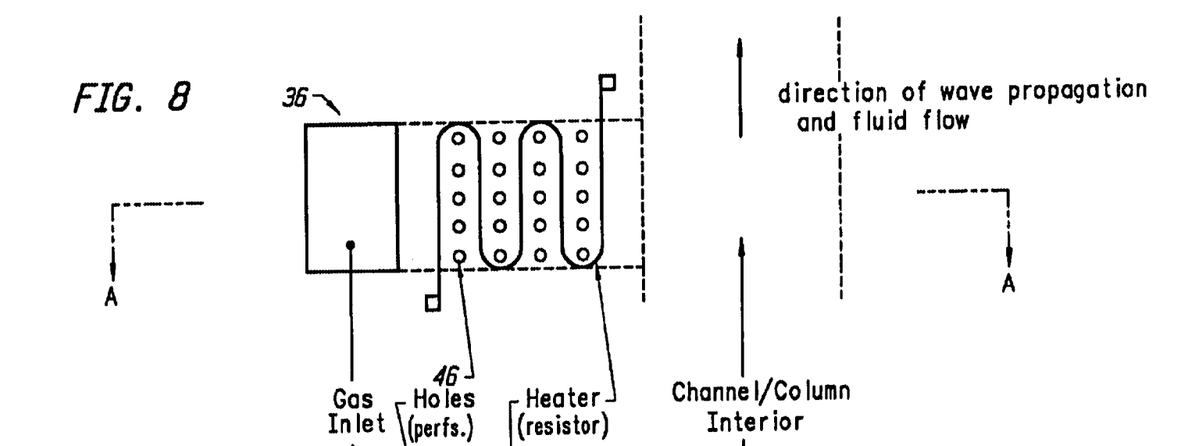
FIG. 8 illustrates a more detailed view of a gas chromatograph than does FIG. 7 showing an embodiment of a sample injector made from a heated platform with a sorptive material connected to the separation column.
Figure 9:
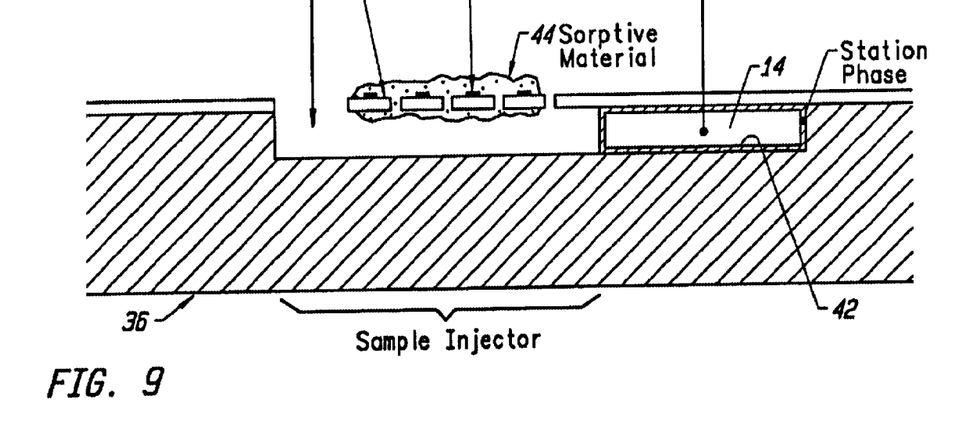
FIG. 9 is a section view taken along the line AA of FIG. 8.

FIG. 7 is a conceptual view of a miniature chromatographic separation system 28 based on use of and incorporating the pump 10. The interdigited fingers 24a, 24b, as illustrated extend along most or all of the length of the separation column 34. A filter or denuder 30 is attached to the inlet 32 of an ultrasonically pumped separation column 34. Also attached to the column 34 is sample injector 36 which is shown in FIGS. 8 and 9. A detector 38 is attached at an outlet end 40 of the column 34. However, they need not extend the entire length of the column 34 since the elastic waves will sustain themselves beyond the last of the fingers. What is important is that each adjacent set of the finger pairs 24a, 24b must not be separated from the next adjacent set of finger pairs 24a, 24b by more than the distance the elastic waves will sustain themselves.

Figure 7A:
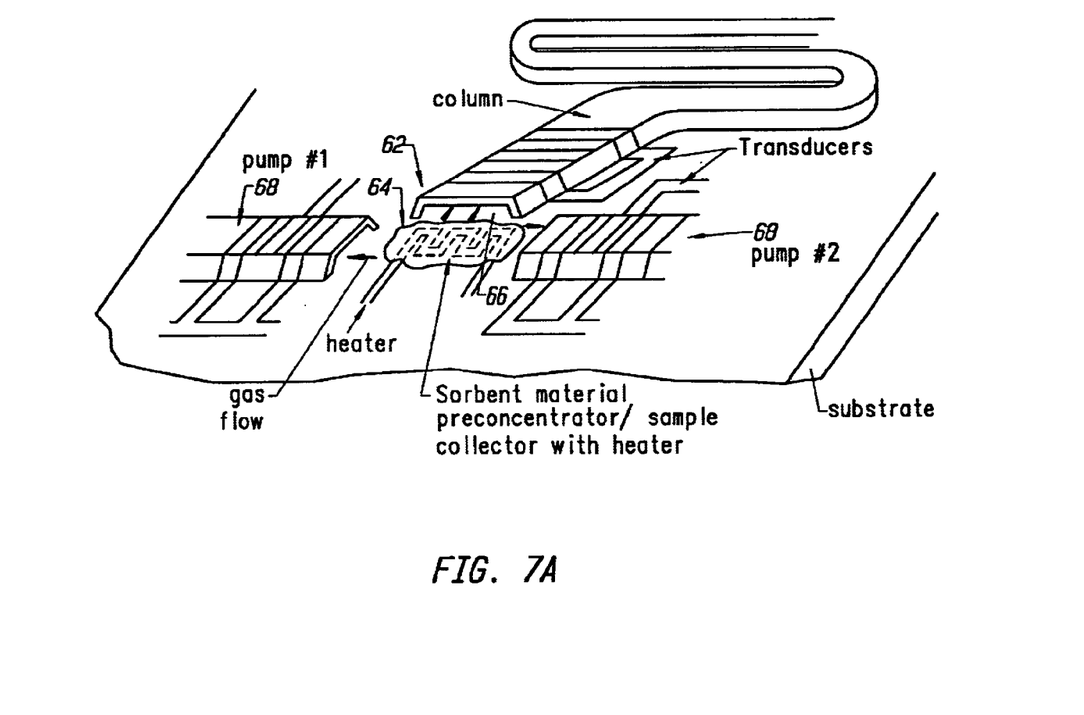

FIG. 7a shows an embodiment of a split sample injector 62 that may be used with the chromatograph or other system. Sorptive sample injector 64 at the inlet 66 of the instrument (e.g., separation column) is also bordered by the inlet of multiple dilution pumps 68. In operation, the dilution pumps are used to draw gas away from the sorptive sample injector as it releases trapped vapors, thereby reducing the amount of sample injected into the instrument at inlet 66.

FIGS. 8 and 9 show more details of a preferred embodiment of micro GC system of FIG. 7. It will be noted that the column interior 42 is coated with a stationary phase 44 of sorptive material on one or more walls. The stationary phase extends substantially all of the column length. Attached to the column 34 is the sample injector 36. The sample injector is composed of a sorptive material 45, which may be a polymer or particulate material such as Tenax or Carbopack, and a heater 46 for releasing compounds that have been trapped by the sorptive material.

Figure 10:
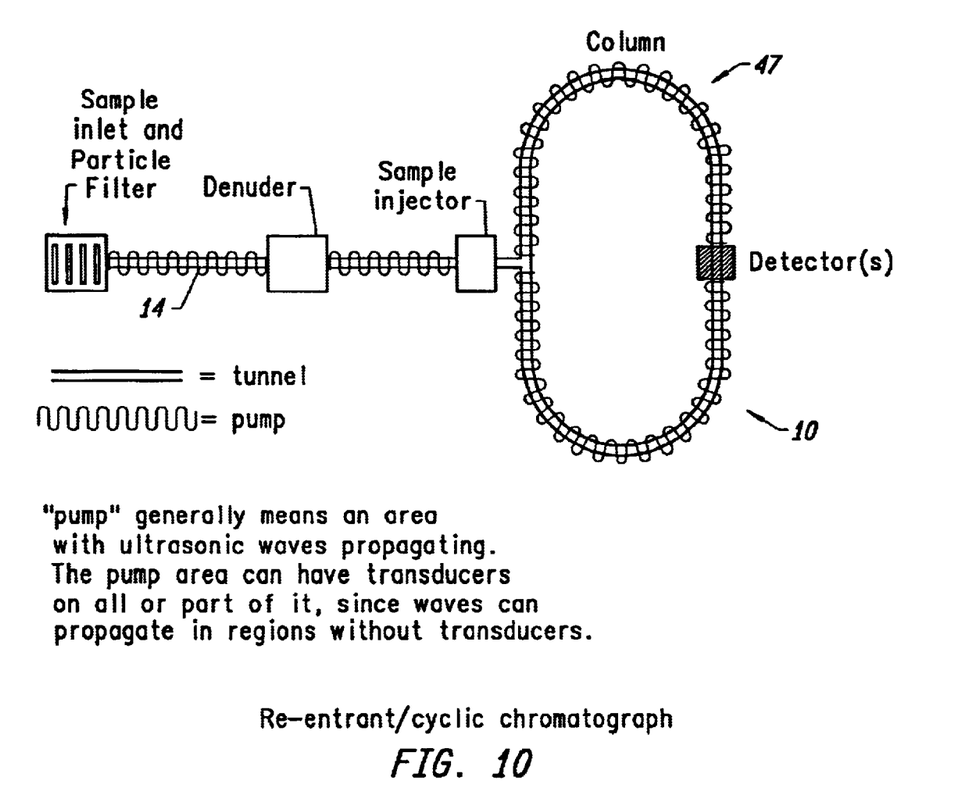
FIG. 10 is a cyclic chromatograph.

FIG. 10 shows cyclic or re-entrant chromatographic system based on pump 10. Ultrasonically-pumped column 47 forms a closed loop in which samples can be recirculated multiple times to increase the effective column length and obtain higher resolution of separation. Any desired resolution can be achieved in situ by monitoring the detector output each time the sample completes the loop. This design can use a shorter column than required by a non-reentrant design, which aids in reducing the size of the system. The rest of system is similar to FIGS. 8 and 9.

Figure 11:
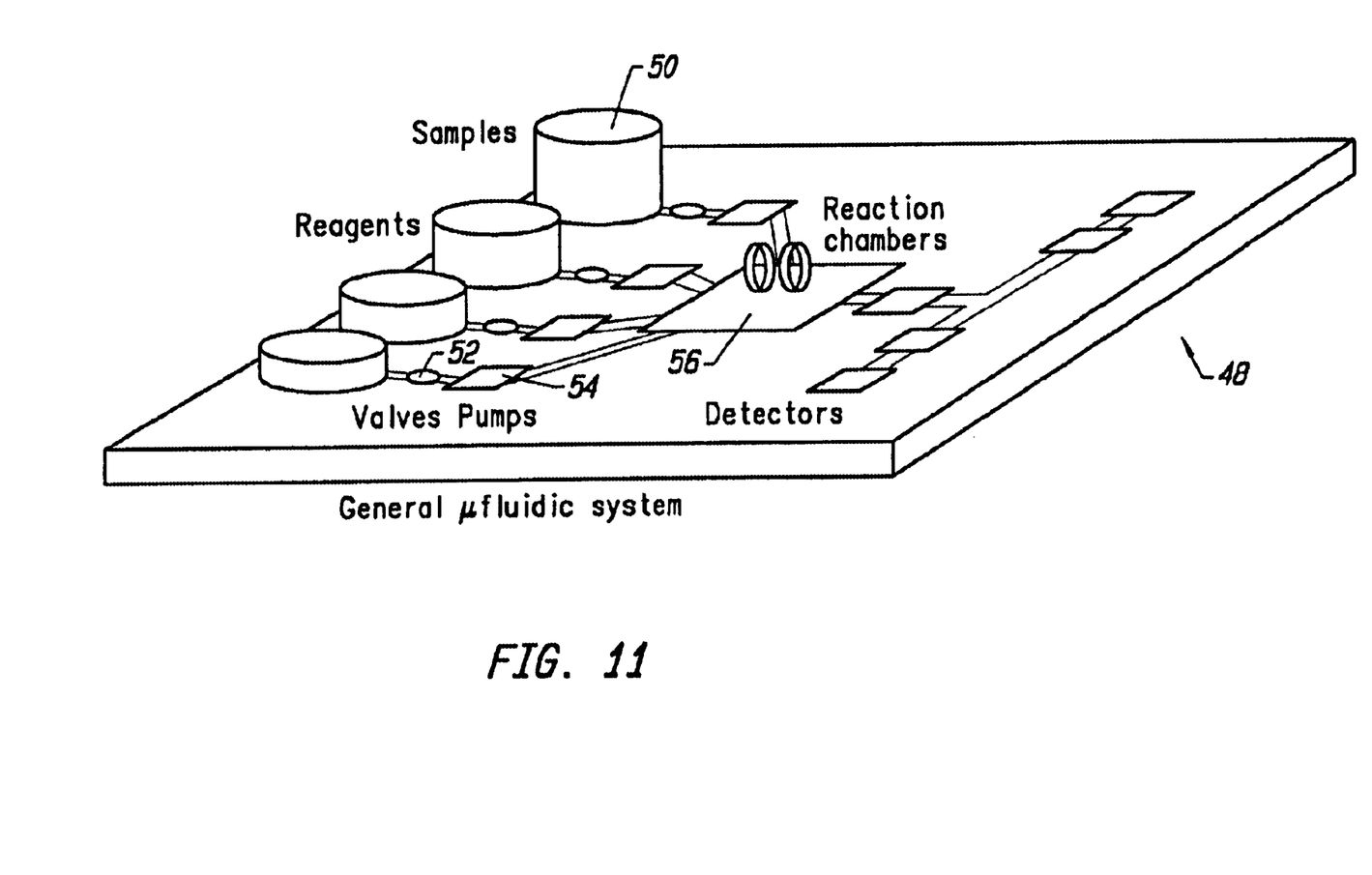
FIG. 11 illustrates, in schematic format, a fluidic microsystem based on a pump in accordance with one or more embodiments of the invention.

FIG. 11 conceptually shows a general microfluidic system 48 based on the pump 10. Sample receptacles 50, valves 52, pumps 54 and reaction chambers 56 are illustrated. This type of system may be used for a variety of purposes, such as to automate tests for biochemical warfare agents and diseases, mix and deliver drugs, pre-process environmental and industrial samples for analysis by micro or macro analytical instruments. As only one example of many the system can be used to carry out microscale PCR procedures as described above. The system can also be used for any of many chemical, physical and/or biological analysis and/or reaction techniques as discussed in detail above. Delivery of drugs, etc. from an implanted device to a desired location in a patient is also attainable.

INDUSTRIAL APPLICABILITY

The present invention provides a micro sized pump 10 and pumping system useful, inter alia, to pump materials from one place to another whereby micro chemical and biological analysis can be carried out in the field on very small samples.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A chromatographic column comprising a micro sized pump, the pump comprising:
   a substrate which at least partially defines one or more walls of a longitudinally extending tunnel, wherein the walls of the tunnel are coated with a stationary phase, the tunnel having a vibratable wall portion;
   a sonic energy generator positioned in sonic energy transmitting relation to the vibratable wall portion, the sonic energy generator being adapted to generate elastic waves which travel along the longitudinal extension of the tunnel; and
   means for limiting the elastic waves such that they travel in substantially only a single direction.

2. The chromatographic column of claim 1, wherein the tunnel has a maximum lateral dimension of less than about 500 microns.

3. The chromatographic column of claim 1, wherein the generator is in the nature of a first plurality of substantially parallel conductors, each one of which is in electrical conducting relation to each other, and a second plurality of substantially parallel conductors, each one of which is in electrical conducting relation to each other, the first and second pluralities of conductors being electrically isolated from one another, the conductors of the first and second pluralities of conductors being interdigitally arranged with one another and extending along the longitudinal extension of the tunnel.

4. The chromatographic column of claim 3, wherein the interdigitally arranged conductors are spaced from one another within a distance of no more than that over which the elastic waves sustain themselves.

5. The chromatographic column of claim 1, wherein the tunnel is in the nature of a trench extending into the substrate and the vibratable wall portion comprises a plate which covers the trench.

6. The chromatographic column of claim 5, wherein the trench includes a piezoelectric layer.

7. The chromatographic column of claim 6, wherein the piezoelectric layer is zinc oxide, aluminum nitride, lead zirconate titanate, barium titanate or lithium niobate.

8. A chromatographic column as set forth in claim 1, wherein the stationary phase is a polymer.

9. A chromatographic column as set forth in claim 1, wherein the stationary phase is a self-assembled monolayer.

10. A analysis system comprising the chromatographic column of claim 1, a sample injector and a detector.

11. An analysis system as set forth in claim 10, wherein the detector is an ultrasonic sensor.

12. An analysis system as set forth in claim 10, wherein the sample injector includes a heated platform along with a sorptive material.

13. A chemical or biological analysis system comprising a micro sized pump in combination with a sensor,
   wherein the pump comprises:
      a substrate which at least partially defines one or more walls of a longitudinally extending tunnel, the tunnel having a vibratable wall portion;
      a sonic energy generator positioned in sonic energy transmitting relation to the vibratable wall portion, the sonic energy generator being adapted to generate elastic waves which travel along the longitudinal extension of the tunnel; and
      means for limiting the elastic waves such that they travel in substantially only a single direction, and
   wherein the sensor is connected to receive a sample having one or more components pumped via the tunnel and to measure a quantity indicative of at least one of the components.

14. An analysis system as set forth in claim 13, including one or more additional sensors, each being connected to receive the sample pumped via the tunnel and to measure an additional quantity indicative of at least one of the components.

15. A chemical or biological reaction system comprising one or more micro sized pumps in combination with a reaction region, wherein the one or more microsized pumps each comprise:
   a substrate which at least partially defines one or more walls of a longitudinally extending tunnel, the tunnel having a vibratable wall portion;
   a sonic energy generator positioned in sonic energy transmitting relation to the vibratable wall portion, the sonic energy generator being adapted to generate elastic waves which travel along the longitudinal extension of the tunnel; and
   means for limiting the elastic waves such that they travel in substantially only a single direction, wherein the reaction region is adjacent the substrate and is connected to receive a reaction sample having one or more reactants pumped via the tunnel(s) and to carry forth a reaction thereat to thereby form a reacted sample.

16. A reaction system as set forth in claim 15 including an additional reaction region, the additional reaction region being connected to receive the reacted sample pumped via a selected one of the one or more of the tunnels and to carry forth an additional reaction thereat to thereby form a further reacted sample.

17. A reaction system as set forth in claim 16 wherein the additional reaction region is connected to receive an additional reactant for reaction with the reacted sample thereat to thereby form the further reacted sample.

* * * * *